United States Patent
Goda et al.

(10) Patent No.: US 8,968,612 B2
(45) Date of Patent: Mar. 3, 2015

(54) MANUFACTURING DEVICE AND MANUFACTURING METHOD FOR ABSORBENT

(75) Inventors: Hidefumi Goda, Kagawa (JP); Kenji Takeuchi, Kagawa (JP); Hiroki Yamamoto, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 106 days.

(21) Appl. No.: 13/637,145

(22) PCT Filed: Mar. 17, 2011

(86) PCT No.: PCT/JP2011/056367
§ 371 (c)(1),
(2), (4) Date: Nov. 20, 2012

(87) PCT Pub. No.: WO2011/118492
PCT Pub. Date: Sep. 29, 2011

(65) Prior Publication Data
US 2013/0062802 A1  Mar. 14, 2013

(30) Foreign Application Priority Data
Mar. 26, 2010 (JP) .................................. 2010-072535

(51) Int. Cl.
*A61F 13/15* (2006.01)
*B29B 17/00* (2006.01)

(52) U.S. Cl.
CPC ....... *A61F 13/15658* (2013.01); *B29B 17/0005* (2013.01)
USPC .................. 264/37.29; 264/517; 425/80.1

(58) Field of Classification Search
None
See application file for complete search history.

(56) References Cited

U.S. PATENT DOCUMENTS

| | | | |
|---|---|---|---|
| 4,495,119 A * | 1/1985 | Chung | 264/37.28 |
| 4,551,191 A | 11/1985 | Kock et al. | |
| 4,610,678 A | 9/1986 | Weisman et al. | |
| 4,950,444 A * | 8/1990 | Deboufie et al. | 264/37.28 |
| 5,017,324 A | 5/1991 | Kaiser et al. | |
| 5,102,585 A * | 4/1992 | Pieper et al. | 264/37.29 |

(Continued)

FOREIGN PATENT DOCUMENTS

CN     1303255 A     7/2001

(Continued)

OTHER PUBLICATIONS

International Search Report based on PCT application No. PCT/JP2011/056367 dated Apr. 12, 2011 (4 pgs).
Chinese Office Action from corresponding Chinese application No. 201180016238.8 dated Feb. 8, 2014 ((4 pgs).
European extended Search Report from corresponding European application No., 11759298.0 dated 06/168/2014 (10 pgs).

*Primary Examiner* — Mary F Theisen
(74) *Attorney, Agent, or Firm* — Brinks Gilson & Lione

(57) ABSTRACT

An absorbent manufacturing device forms an absorbent by depositing a liquid absorbent fiber and a super absorbent polymer in a deposition part. The absorbent manufacturing device includes: a plurality of suction holes that are provided in the deposition part, wherein the liquid absorbent fiber and the super absorbent polymer flowing inside a scattering duct are deposited in the deposition part by suction; a suction duct that is provided in communication with the suction holes and draws air so that the suction holes perform suction; and a separator that separates a super absorbent polymer of size equal to or larger than a certain size from a flow of air flowing in the suction duct and returns the separated super absorbent polymer to the scattering duct.

2 Claims, 5 Drawing Sheets

(56) References Cited

U.S. PATENT DOCUMENTS

| | | |
|---|---|---|
| 6,033,199 A | 3/2000 | Vonderhaar et al. |
| 6,646,180 B1 | 11/2003 | Chmielewski |
| 6,802,353 B2 * | 10/2004 | Malakouti et al. ............ 156/433 |
| 2006/0005919 A1 | 1/2006 | Schewe et al. |

FOREIGN PATENT DOCUMENTS

| | | |
|---|---|---|
| JP | 2004-500165 A | 1/2004 |
| JP | 2008-154964 | 7/2008 |
| JP | 2009-112347 | 5/2009 |
| WO | WO 2007/111873 A2 | 10/2007 |

* cited by examiner

VIEW ALONG ARROWS B-B

MANUFACTURING DEVICE AND MANUFACTURING METHOD FOR ABSORBENT

RELATED APPLICATION

The present application is a 35 U.S.C. §371 national stage filing of International Patent Application No. PCT/JP2011/056367, filed Mar. 17, 2011, to which priority is claimed under 35 U.S.C. §120 and through which priority is claimed under 35 U.S.C. §119 to Japanese Priority Patent Application No. 2010-072535, filed Mar. 26, 2010.

TECHNICAL FIELD

The present invention relates to a manufacturing method and a device for manufacturing an absorbent of an absorbent article such as a disposable diaper.

BACKGROUND ART

Conventional disposable diapers and the like are known as absorbent articles that absorb liquids such as excreted fluids. An absorbent article includes an absorbent that absorbs liquids, as a component part.

The absorbent has a liquid absorbent fiber, such as pulp fiber, formed into a specified shape as a base material with particulates of a super absorbent polymer mixed therein. A super absorbent polymer, which is referred to hereinbelow as "SAP," is a high molecular weight polymer and the like that swells due to liquid absorption and demonstrates good liquid retention capacity.

This type of absorbent is formed by depositing, for example, a pulp fiber in an air flow flowing through an appropriate scattering duct onto a deposition part on the outer surface of a rotating drum. Specifically, the deposition part has multiple suction holes provided in a specific arrangement pattern. The pulp fiber is deposited by suction of the suction holes in a shape having substantially the outline of the deposition part and the absorbent is formed.

A nozzle for supplying the SAP is also arranged inside the scattering duct and the SAP is discharged into the scattering duct from the nozzle. Accordingly, the SAP is also carried by the air flow inside the scattering duct and deposited in the deposition part along with the pulp fiber.

CITATION LIST

Patent Literature

[PTL 1] JP 2009-112347A

SUMMARY OF INVENTION

Technical Problem

A portion of the SAP is not deposited in the deposition part but instead passes through the suction holes as-is and is discarded. However, SAP is very expensive compared to pulp fiber. Therefore, in order to reduce manufacturing costs, SAP cannot be wastefully discarded.

On the other hand, the suction of the abovementioned suction holes is produced by the intake of air by a suction duct communicating with the suction holes. Consequently, the SAP that passes through the suction holes passes through the suction duct. Therefore, if the SAP in the air flowing inside the suction duct is separated and recovered and re-supplied to the scattering duct, The yield factor of SAP may be improved.

Moreover, when the SAP is mixed in the flow of air that passes through the suction duct, the lifespan of the suction duct will be shortened due to collisions by the SAP. However, this point may also be remedied if the SAP is recovered from the flow of air inside the suction duct as described above.

However, if all of the SAP flowing inside the suction duct is returned to the scattering duct, there is a concern that an absorbent will be manufactured that will cause absorption defects when the absorbent article is used.

Specifically, the center value of the SAP particle diameter is generally established to be 300 to 500 microns. In reality, the SAP particles grind against each other in the process of being supplied to the scattering duct and the like; as a result, especially small particles (hereinbelow referred to as "SAP powder") of sizes (e.g., particle diameters of 10 microns or less) that are smaller than the abovementioned range of values are generated. This SAP powder then enters gaps between the fibers of the absorbent pulp fibers and fills the gaps.

Ideally during the initial stage of liquid absorption, the liquid gradually enters the gaps between the fibers in the absorbent to ensure smooth liquid absorption. However, if these gaps are filled with SAP powder, the liquid does not enter the gaps and liquid absorption cannot be carried out.

Thus, in consideration of this point, the embedding action in the gaps between the fibers by the SAP powder is facilitated when all the SAP flowing in the suction duct is recovered and returned to the scattering duct as described above, and as a result, there is a concern that an absorbent in which liquid absorption obstruction easily occurs will be manufactured.

In view of the conventional problems described above, an advantage of the present invention is to manufacture an absorbent which can suppress the obstruction of liquid absorption during the initial stage of liquid absorption and to increase the yield factor of SAP and the lifespan of the suction duct.

Solution to Problem

A primary aspect of the invention for achieving the abovementioned object is an absorbent manufacturing device for forming an absorbent by depositing a liquid absorbent fiber and a super absorbent polymer in a deposition part, the device comprising:

a plurality of suction holes that are provided in the deposition part and cause the liquid absorbent fiber and the super absorbent polymer to be deposited in the deposition part by suction, the liquid absorbent fiber and the super absorbent polymer flowing inside a scattering duct;

a suction duct that is provided in communication with the suction holes and draws air so that the suction holes perform suction; and a separator that separates a super absorbent polymer of size equal to or larger than a certain size from a flow of air flowing in the suction duct and returns the separated super absorbent polymer to the scattering duct.

Furthermore, an absorbent manufacturing method for forming an absorbent by depositing a liquid absorbent fiber and a super absorbent polymer in a deposition part comprises:

depositing the liquid absorbent fiber and the super absorbent polymer in the deposition part by suction from a plurality of suction holes, the suction holes being provided in the deposition part, the liquid absorbent fiber and the super absorbent polymer flowing inside a scattering duct; and when the suction holes suck an air by suction of the air of a suction duct that is provided in communication with the suction holes, separating a super absorbent polymer of size equal to or larger than a certain size from an air flowing through the suction duct and returning the separated super absorbent polymer to the scattering duct.

Other features of the present invention will be understood from the specification and the accompanying drawings.

Advantageous Effects of Invention

According to the present invention, it is possible to manufacture an absorbent which can suppress the obstruction of liquid absorption during the initial stage of liquid absorption and to increase the yield factor of SAP and the lifespan of the suction duct.

BRIEF DESCRIPTION OF DRAWINGS

FIG. 1A is a plan view and FIG. 1B is a side view along arrows B-B in FIG. 1A.

DESCRIPTION OF EMBODIMENTS

Figure 1A:
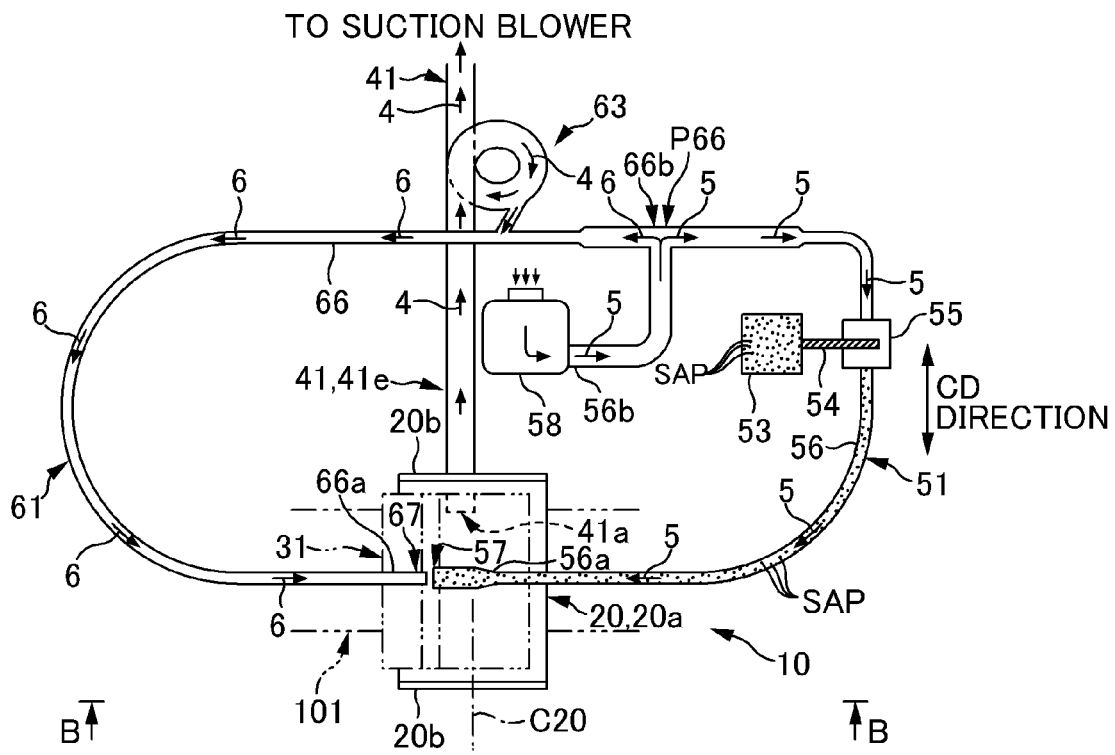
FIGS. 1A and 1B are overall layouts of a manufacturing device 10 of an absorbent 1 according to the present embodiment.

The following examples will become evident at least through the specification and the accompanying drawings.

An absorbent manufacturing device for forming an absorbent by depositing a liquid absorbent fiber and a super absorbent polymer in a deposition part comprises:

a plurality of suction holes that are provided in the deposition part and cause the liquid absorbent fiber and the super absorbent polymer to be deposited in the deposition part by suction, the liquid absorbent fiber and the super absorbent polymer flowing inside a scattering duct;

a suction duct that is provided in communication with the suction holes and draws air so that the suction holes perform suction; and a separator that separates a super absorbent polymer of size equal to or larger than a certain size from a flow of air flowing in the suction duct and returns the separated super absorbent polymer to the scattering duct.

According to this absorbent manufacturing device, SAP that passes through the suction holes without being deposited in the deposition part and flows in the suction duct can be captured and re-supplied to the deposition part. This can improve the yield factor of SAP, which is expensive compared to the liquid absorbent fiber.

Additionally, the amount of SAP that passes through the suction duct located downstream from the separator is reduced. Consequently, the lifespan of the suction duct is increased.

Furthermore, SAP of size equal to or larger than a certain particle size is separated from the SAP flowing inside the suction duct and returned to the scattering duct. This enables to effectively prevent SAP powder from being re-supplied to the scattering duct. Therefore, the manufacturing of an absorbent that suppresses the obstruction of liquid absorption during the initial stage of liquid absorption can be achieved.

In the above absorbent manufacturing device, it is preferable that the separator is a centrifugal separator.

According to this absorbent manufacturing device, because the separator is a centrifugal separator, clogging is less likely to occur. Moreover, maintenance works caused by clogging can be reduced.

In the above absorbent manufacturing device, it is preferable that the centrifugal separator includes a flow channel that is provided as a part of the suction duct and that turns spirally, a branched path that is a branch of the flow channel is provided in an portion of the flow channel radially outwardly with respect to a turning-radius direction, by a centrifugal force that acts while flowing through the flow channel, the super absorbent polymer of size equal to or larger than the certain size is moved toward the portion of the flow channel and is guided into the branched path; and the super absorbent polymer of size equal to or larger than the certain size is fed to the scattering duct through the branched path.

According to this absorbent manufacturing device, the SAP of size equal to or larger than the certain size can be captured with a simple configuration including the spiral flow channel and the branched path. Consequently, the manufacturing device can be achieved with a low cost and cost reductions for the absorbent article using the absorbent can be achieved.

Furthermore, an absorbent manufacturing method for forming an absorbent by depositing a liquid absorbent fiber and a super absorbent polymer in a deposition part, comprises:

depositing the liquid absorbent fiber and the super absorbent polymer in the deposition part by suction from a plurality of suction holes, the suction holes being provided in the deposition part, the liquid absorbent fiber and the super absorbent polymer flowing inside a scattering duct; and when the suction holes suck an air by suction of the air of a suction duct that is provided in communication with the suction holes, separating a super absorbent polymer of size equal to or larger than a certain size from an air flowing through the suction duct and returning the separated super absorbent polymer to the scattering duct.

According to this absorbent manufacturing device, SAP that passes through the suction holes without being deposited in the deposition part and flows in the suction duct can be captured and re-supplied to the deposition part. This can improve the yield factor of SAP, which is expensive compared to the liquid absorbent fiber.

Additionally, the amount of SAP that passes through the suction duct located downstream from the position in which the super absorbent polymer is separated is reduced. Consequently, the lifespan of the suction duct is increased.

Furthermore, SAP of size equal to or larger than a certain particle size is separated from the SAP flowing inside the suction duct and returned to the scattering duct. This enables to effectively prevent SAP powder from being re-supplied to the scattering duct. Therefore, the manufacturing of an absorbent that suppresses the obstruction of liquid absorption during the initial stage of liquid absorption can be achieved.

Present Embodiment

Figure 1B:
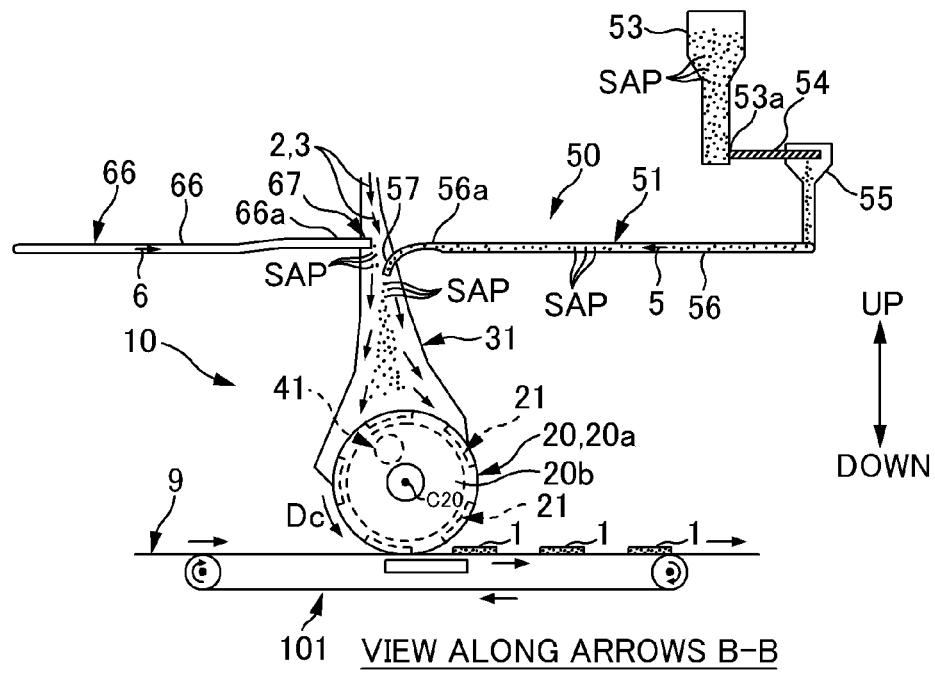

FIGS. 1A and 1B are overall layouts of a manufacturing device 10 of an absorbent 1 according to the present embodiment. FIG. 1A is a plan view and FIG. 1B is a side view along arrows B-B in FIG. 1A. For illustrative reasons, some portions in FIGS. 1A and 1B are shown as transparent or in a sectional view.

As illustrated in FIG. 1B, the manufacturing device 10 is a so-called fiber deposition device 10. Specifically, the manufacturing device 10 includes: a rotating drum 20 that rotates in a circumferential direction Dc and is provided with concave forming molds 21 (corresponding to the deposition part) on an outer circumferential surface 20a; a scattering duct 31 in which a pulp fiber 2 is deposited to form an absorbent 1 in the forming molds 21 by scattering the pulp fiber 2 toward the outer circumferential surface 20a of the rotating drum 20; a SAP supply device 50 that supplies SAP to the forming mold 21 through the scattering duct 31; and a conveyor belt 101 that is provided further downstream in the circumferential direction Dc than the installation position of the scattering duct 31, separates the absorbent 1 from the forming mold 21 and transports the absorbent 1.

Hereinbelow, the circumferential direction Dc of the rotating drum 20 is referred to simply as "circumferential direction Dc," and the width direction of the rotating drum 20 is referred to as "CD direction."

Figure 2:
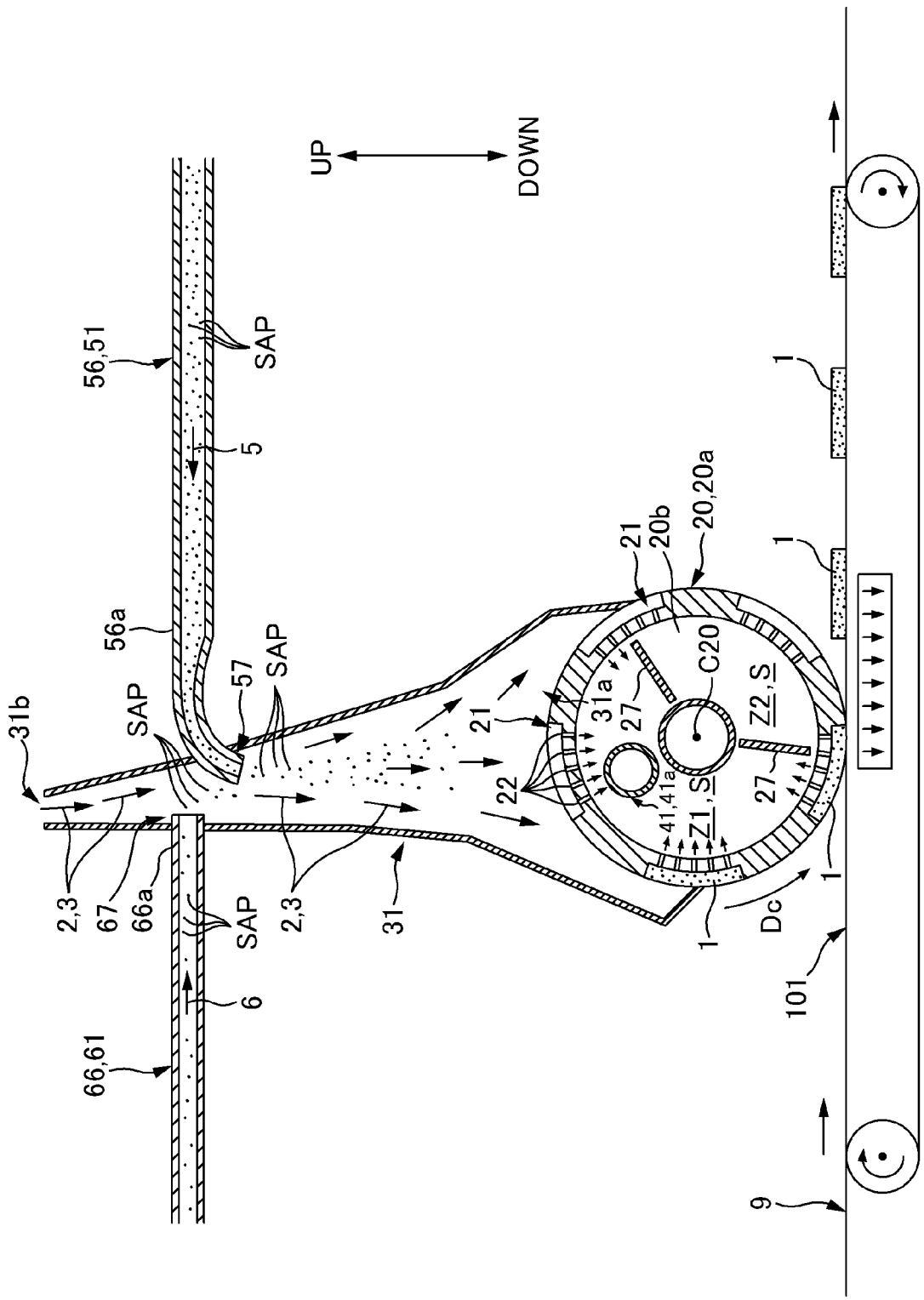
FIG. 2 is an enlargement of a center vertical sectional view of a rotating drum 20.

FIG. 2 is an enlarged side view of the rotating drum 20.

The rotating drum 20 has a cylindrical body that is rotated around a rotating shaft C20 that is, for example, horizontal to the CD direction. Openings at the either end of the rotating drum 20 in the width direction are covered and capped by a pair of circular walls 20b and 20b (FIGS. 1A and 1B). Consequently, a substantially closed space S having a donut shape is defined on an inner side of the rotating drum 20.

The abovementioned forming molds 21, 21, . . . are provided on the outer circumferential surface 20a of the rotating drum 20 at a certain pitch in the circumferential direction Dc. The bottom surfaces of the forming molds 21 have multiple suction holes 22, 22, . . . . Through these suction holes 22, 22, . . . , the substantially closed space S communicates with the inside of the forming molds 21, allowing the passage of air.

The substantially closed space S is divided into zones in the circumferential direction Dc by partition walls 27 and 27 as illustrated in FIG. 2. A first zone Z1 illustrated in FIG. 2 is connected to a suction duct 41 and air is sucked into the first zone Z1 through suction openings 41a of the suction duct 41 to maintain the first zone Z1 at a negative pressure state in which the air pressure is lower than the external pressure.

Consequently, the suction holes 22 of the forming molds 21 suck air when the forming molds 21 move to a position on the outer circumferential surface 20a corresponding to the first zone Z1. As a result, the pulp fiber 2 and the SAP in the scattering duct 31 are deposited in the forming molds 21 to form the absorbent 1.

The suction duct 41 is not connected to another second zone Z2, thus when the forming molds 21 enter a position on the outer circumferential surface 20a corresponding to the second zone Z2, the suction in the forming molds 21 is substantially stopped. The absorbent 1 in the forming molds 21 is passed on to the conveyor belt 101 due to suction from the conveyor belt 101, the conveyor belt 101 being arranged in correspondence with the second zone Z2. Then, the absorbent 1 is transported to a subsequent process by the conveyor belt 101.

Meanwhile, as illustrated in FIG. 2, a sheet component 9 such as tissue paper or a non-woven fabric may be supplied on the conveyor belt 101 so that the absorbent is passed on to the sheet component 9. In this case, the sheet component 9 becomes an outer surface sheet (sheet that comes into contact with the skin of the wearer), etc of a disposable diaper or a sanitary napkin.

As illustrated in FIG. 2, the scattering duct 31 is, for example, a tubular member having a substantially rectangular cross-section which is disposed above the rotating drum 20; the tubular axis of the scattering duct 31 is oriented in a substantially vertical direction. The scattering duct 31 has a scattering opening 31a at the bottom end and the opening 31a covers a certain range in the circumferential direction Dc of an upper portion of the outer circumferential surface 20a of the rotating drum 20. From an upper end opening 31b that is at the end opposite from the scattering opening 31a, the pulp fiber 2 is supplied; the pulp fiber 2 is formed by grinding a pulp sheet with a grinder (not illustrated). The supplied pulp is combined with the sucked air from the aforementioned suction holes 22, and an air flow 3 including the pulp fiber 2 is formed inside the scattering duct 31 flowing from the top toward the bottom. As a result, the pulp fiber 2 and the SAP are deposited in the forming molds 21 to form absorbents 1 as described above when the forming molds 21 pass the position of the scattering opening 31a due to the rotation of the rotating drum 20.

As illustrated in FIGS. 1A and 1B, the SAP supply device 50 has a dual supply system including: a normal supply system 51 that supplies fresh SAP to the scattering duct 31; and a recovery supply system 61 that recovers SAP with a relatively large particle size from an air flow 4 (corresponding to the flow of air) flowing in the suction duct 41 and re-supplies the recovered SAP to the scattering duct 31. The provision of the latter recovery supply system 61 results in improvement of the yield factor of the SAP and the long lifespan of the suction duct 41. In addition thereto, it is possible to manufacture the absorbent 1 that suppresses the obstruction of liquid absorption.

The normal supply system 51 includes: a hopper 53 that is a reservoir for accumulating the fresh SAP; a screw feeder 54 that feeds regular amounts of the SAP from the hopper 53 and is provided in communication with a bottom opening 53a of the hopper 53; a chute 55 that stops the SAP supplied by dropping from the screw feeder 54 and causes the SAP to slide down; and a SAP supply path 56 formed as a tube suitable for feeding, under pressure, the SAP that slides down from the chute 55 toward the scattering duct 31.

At one tube end 56a of the SAP supply path 56, a nozzle 57 that acts as a SAP discharge port is disposed; the nozzle 57 is arranged inside the scattering duct 31. On the other hand, another tube end 56b of the SAP supply path 56 is connected to a blower 58. Due to ventilation from the blower 58, an air flow 5 blowing from the other tube end 56b toward the nozzle 57 is generated in the SAP supply path 56. The abovementioned chute 55 is provided at an intermediate location in the SAP supply path 56. Consequently, the SAP supplied by sliding down from the chute 55 is fed under pressure toward the scattering duct 31 through the SAP supply path 56 and the nozzle 57.

The recovery supply system 61 includes: a centrifugal separator 63 that is an example of separator that recovers the SAP from the air flow 4 in the suction duct 41; and a re-supply path 66 that re-supplies the SAP recovered by the centrifugal separator 63 toward the scattering duct 31.

The re-supply path 66 is formed as a suitable pipe and is provided with a nozzle 67 at one tube end 66a. The nozzle 67 is arranged inside the scattering duct 31. On the other hand, another tube end 66b of the re-supply path 66 is connected to a position P66 that is upstream from the chute 55 in the abovementioned SAP supply path 56. As a result, an air flow 6 flowing toward the nozzle 67 is generated inside the re-supply path 66 due to the ventilation from the blower 58. Consequently, the SAP recovered with the centrifugal separator 63 is fed under pressure toward the scattering duct 31 through the re-supply path 66 and the nozzle 67 by the air flow 6.

Figure 3:
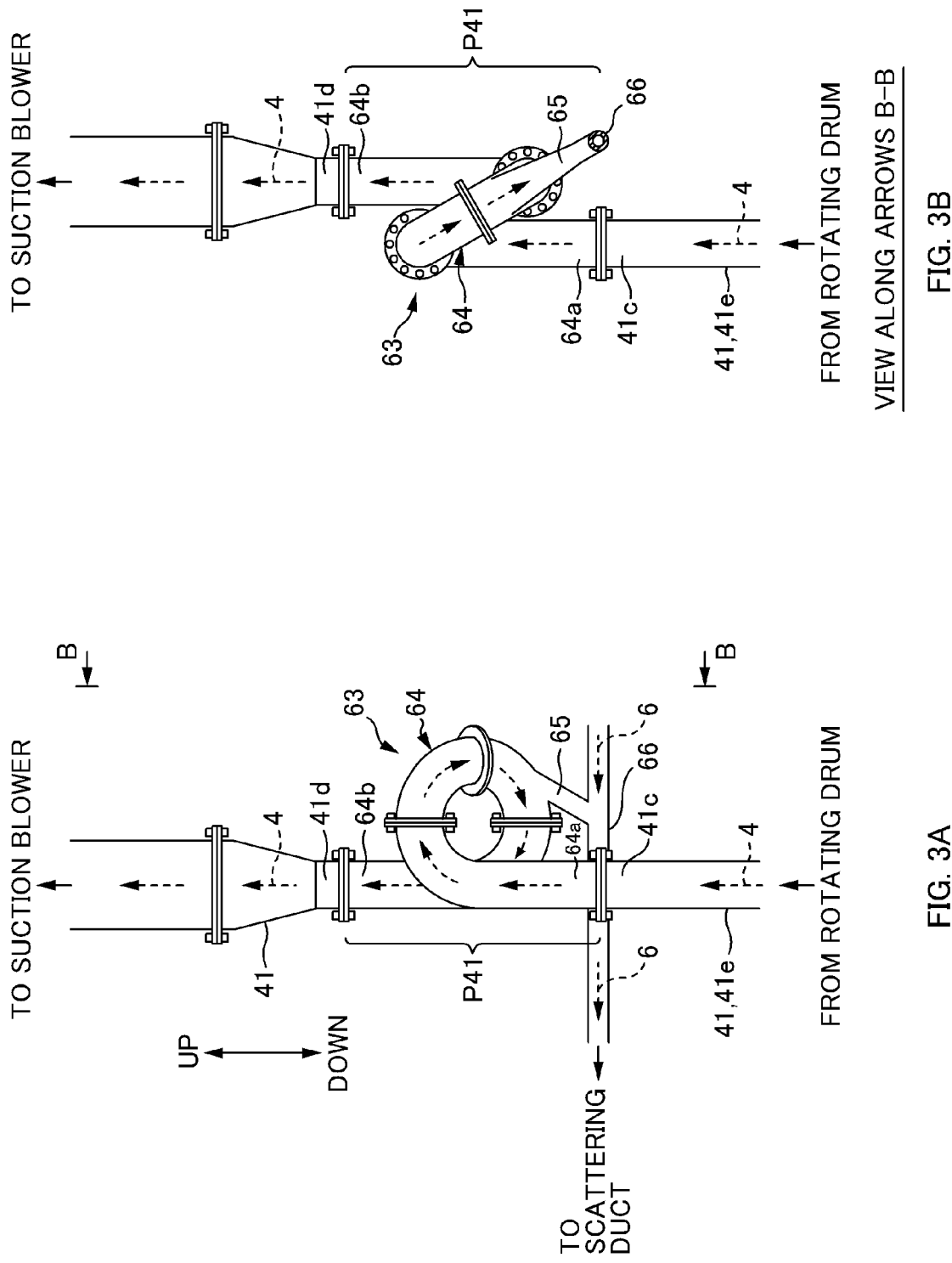
FIG. 3A is a side view of a centrifugal separator 63.
FIG. 3B is a view along arrows B-B in FIG. 3A.

FIG. 3A is a side view of the centrifugal separator 63. Moreover, FIG. 3B is a view along arrows B-B in FIG. 3A. The centrifugal separator 63 recovers SAP with a particle diameter of, for example, 100 microns (corresponding to "at least a certain size") from the air flow 4 inside the suction duct 41 as illustrated in FIG. 1A. Specifically, SAP and pulp fiber are included in the air flow 4 inside the suction duct 41 and the SAP having a relatively large size with a particle diameter of at least 100 microns is separated and recovered from the air flow 4. As a result, the SAP with a relatively large size that does not include SAP powder is re-supplied to the scattering duct 31.

The reason that the SAP and the pulp fiber are included in the air flow 4 in the suction duct 41 is explained below. Although a majority of the SAP and the pulp fiber is usually deposited in the forming molds 21 of the rotating drum 20 and remains there, some of the SAP and pulp fiber pass through the suction holes 22 of the forming molds 21.

More specifically, the hole size of the suction hole 22 (for example, the hole size of a round hole made by etching and the like or a rectangular hole of a mesh and the like) may be set within the range from 0.15 to 0.6 mm, for example; more preferably, the hole size should be set within the range from 0.17 to 0.37 mm. Consequently, until a certain amount of the pulp fiber is deposited in the forming molds 21 and retains the SAP, the SAP passes through the suction holes 22. Therefore, SAP of a relatively large size of 100 to 600 microns may be included in the air flow 4 in the suction duct 41 in addition to SAP powder.

As described above, the lower limit of the SAP size to be separated from the SAP powder and recovered is defined by particle diameter. However, in some cases, the SAP size may also be defined by another parameter such as particle length. If particle diameter is used to define the SAP size, the lower limit is not limited to the abovementioned 100 microns in particular, and, for example, the same lower limit may be selected from the range of 10 to 500 microns. Hereinbelow, the SAP of a relatively large size to be preferably recovered will be referred to as "large SAP."

As illustrated in FIGS. 3A and 3B, the main body of the centrifugal separator 63 is a spirally wound pipe 64 having a spiral flow path that turns in a helical shape (spirally wound shape). The spirally wound pipe 64 is intermediately placed in a certain position P41 in place of the piping removed from the suction duct 41 at the certain position P41. As a result, the spirally wound pipe 64 constitutes a portion of the flow path of the suction duct 41. Specifically, one end opening 64a of the spirally wound pipe 64 is connected to a pipe end 41c on the upstream side of the suction duct 41; the other end opening 64b is connected to a pipe end 41d on the downstream side of the suction duct 41. Moreover, a branched pipe (corresponding to a branched path) is provided on the outer periphery portion of the spirally wound pipe 64, outer periphery portion being a portion arranged radially outwardly with respect to the turning-radius direction; and the branched pipe 65 is placed along the flow direction of the air flow 4, in other words, along an approximately tangential direction of the outer periphery portion. The branched pipe 65 is connected to the abovementioned re-supply path 66. Thereby, the large SAP that is centrifugally separated is fed toward the re-supply path 66 through the branched pipe 65. This is described more specifically below.

As described above, SAP and pulp fiber are included in the air flow 4 inside the suction duct 41. Consequently, the SAP and the pulp fiber also flow through the spiral flow path of the spirally wound pipe 64. A centrifugal force depending on the turning radius of the spiral flow path then acts on the SAP and the pulp fiber while the SAP and the pulp fiber are flowing through the spiral flow path, so that the SAP and the pulp fiber are moved to the outside in the turning-radius direction. The degree of movement differs according to the amount of the acting centrifugal force. That is, the large SAP with a large mass is moved further to the outside whereas the SAP powder with a low mass and the pulp fiber do not move to the outside very much. As a result, the large SAP is guided toward the branched pipe 65 provided at the outer periphery portion of the spirally wound pipe 64 and is fed toward the re-supply path 66. On the other hand, the SAP powder and the pulp fiber continue flowing in the suction duct due to the small centrifugal force and are collected and discarded by a dust collector (not illustrated) with an exhaust blower (not illustrated) provided at the end of the suction duct 41. Therefore, the large SAP is substantially selectively recovered by centrifugal separation and re-supplied to the scattering duct 31.

Specifications of the spiral flow path such as the turning radius (turning radius around cross-section), the number of windings (approximately one winding in the illustrated example), and the total length may be appropriately determined according to as follows: the flow rate of the air flow 4 flowing in the spiral flow path; the mass distribution of the SAP and the pulp fiber; and the particle diameter (at least 100 microns, herein) of the large SAP to be desirably separated.

As illustrated in FIG. 3A, it is desirable that the branched pipe 65 is connected to a later portion, and, more preferably, is connected to the later end of the spiral flow path. With such a configuration, even if the total length of the spiral flow path is small, the large SAP to be removed can be reliably guided toward an outer position in the turning-radius direction until the large SAP reaches the branched pipe 65, the outer position being the position at which the branched pipe 65 is placed.

Figure 4:
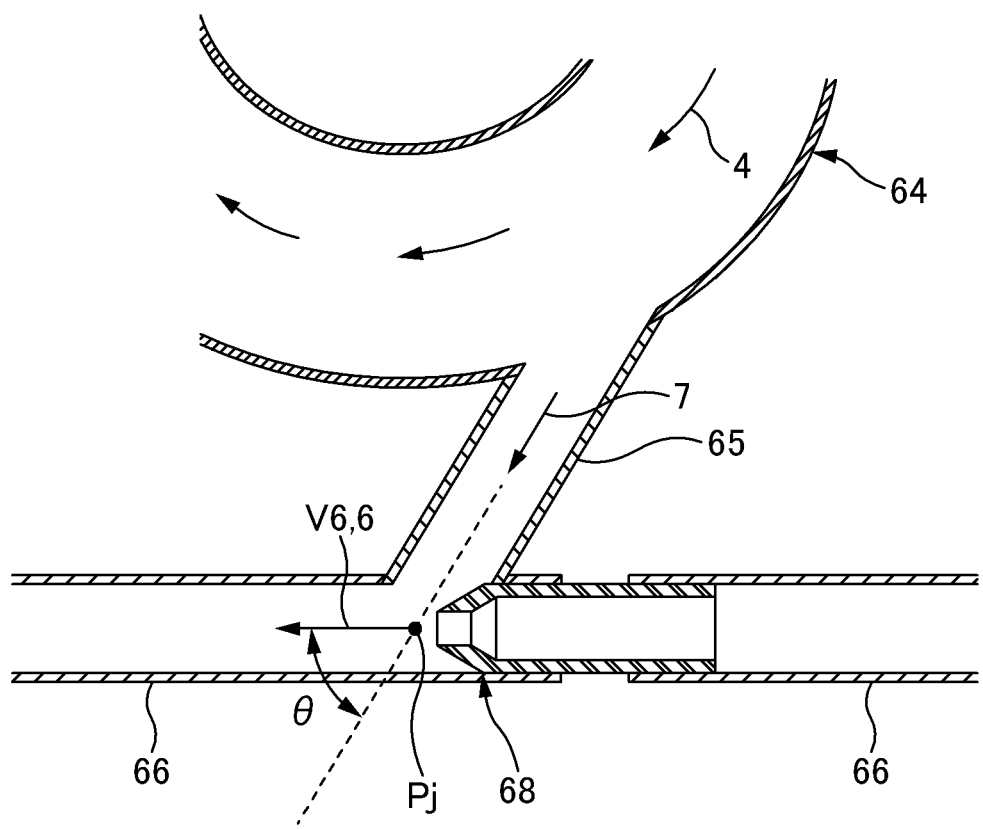
FIG. 4 is an enlarged sectional view of a branched pipe 65 associated with the centrifugal separator 63.

Furthermore, as illustrated in the enlarged cross-section of the branched pipe 65 in FIG. 4, it is desirable that a joint angle (an angle θ formed between the flow directions (pipe axis directions) at a joint position Pj) of the branched pipe 65 and the re-supply path 66 is acute. The joint angle θ is preferably selected from a range between 0 degrees to not more than 80 degrees, or more preferably selected from a range between 0 degrees to not more than 60 degrees.

According to this configuration, the large SAP flowing in the branched pipe 65 can be quickly and smoothly drawn into the re-supply path 66 by the followings: the dynamic pressure of an air flow 6 flowing in the re-supply path 66; the dynamic pressure of an air flow 7 flowing in the branched pipe 65; and an ejector effect based on the viscosity of the air flows 6 and 4. In addition, this drawing effect is improved as a flow rate V6 of the air flow 6 of the re-supply path 66 at the joint position Pj becomes faster. Consequently, in the example illustrated in FIG. 4, a throttle 68 that reduces the flow path cross-section is provided immediately upstream of the joint position Pj of the re-supply path 66, which results in increasing of the flow rate V6 of the air flow 6 at the joint position Pj.

Meanwhile, the reason why the provision of the abovementioned recovery supply system 61 makes it possible to manufacture the absorbent 1 in which j liquid absorption obstruction in the initial stage of liquid absorption will be described below.

First, as previously described, the centrifugal separator 63 recovers the SAP with a particle diameter of, for example, at least 100 microns from the air flow 4 in the suction duct 41. As a result, the SAP having a relatively large size other than SAP powder can be re-supplied to the scattering duct 31.

Consequently, in comparison to a configuration in which all the SAP flowing in the suction duct 41 is collected and re-supplied to the scattering duct 31, this embodiment makes it possible to significantly suppress the obstruction of liquid absorption in the absorbent 1.

Furthermore, as described above, the separator 63 re-supplies the SAP of at least 100 microns to the scattering duct 31. Consequently, the large SAP, that is, the SAP gathered as particles with a relatively large size, is re-supplied to the forming molds 21 via the scattering duct 31, and thus the proportion of the large SAP among the SAP deposited in the absorbent 1 can be increased. This gives the following result: the amount of the SAP powder mixed into the absorbent 1 can be reduced by the increased proportion of the large SAP whereas the total liquid absorption capacity of the SAP, that is, the total amount of the SAP in the absorbent 1 is maintained at a certain amount. Therefore, the absorbent 1 that suppresses the obstruction of liquid absorption during initial liquid absorption can be manufactured.

Figure 5:
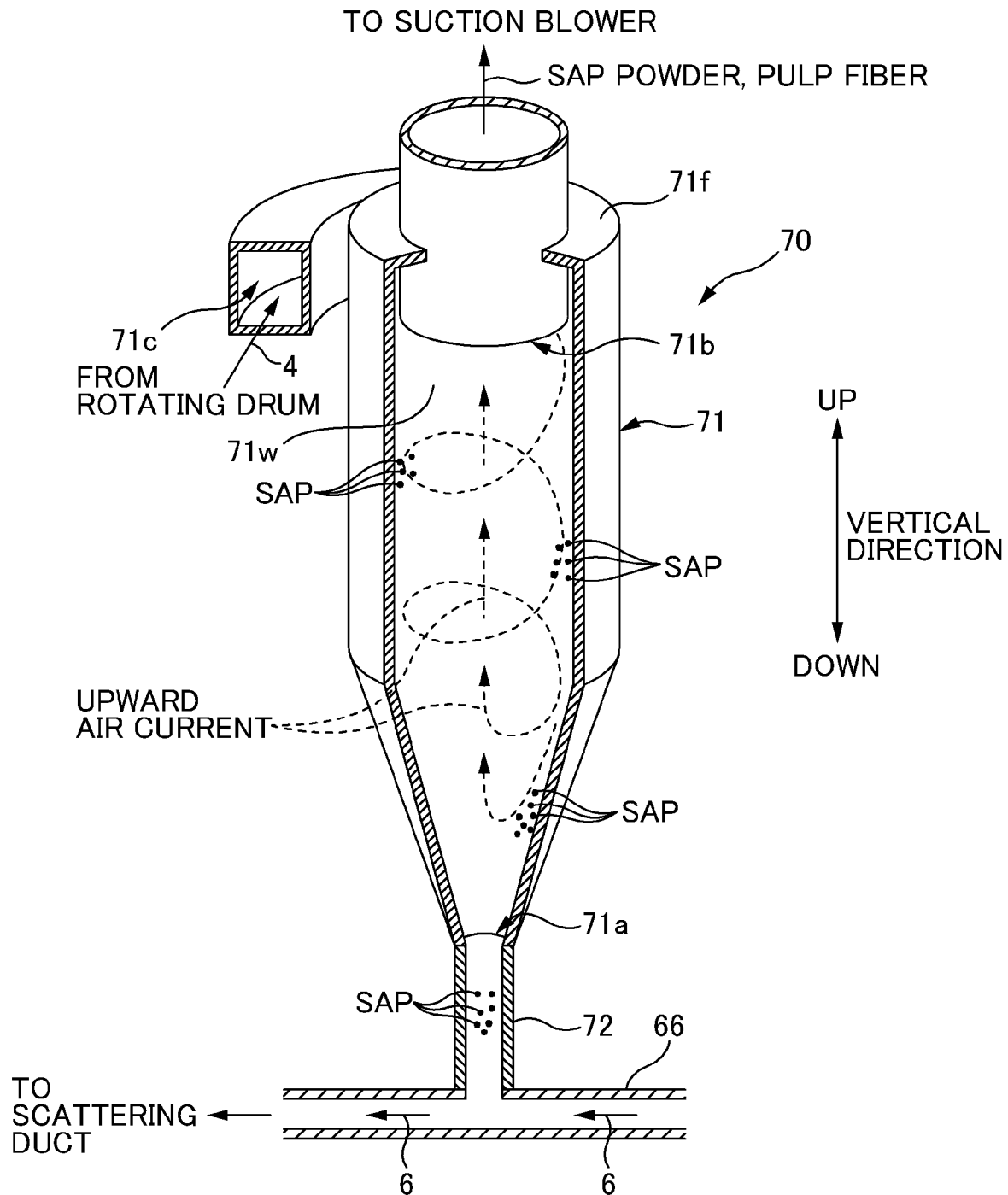
FIG. 5 is a perspective view of a modified example of a separator.

FIG. 5 is a perspective view of a modified example of the separator and is shown with a portion removed. A separator 70 of the modified example is a centrifugal separator but differs from the separator 63 of the previous embodiment in that it uses a cyclone separator. The remaining configuration is roughly the same and thus the following is an explanation only about the cyclone separator 70.

The separator 70 includes a cylindrical body 71 aligned in the vertical direction of the tube axis direction as its main structural component. The lower portion of the cylindrical body 71 has a funnel shape that narrows toward the lowest end thereof. The cylindrical body 71 has a first opening 71a at the lowest end thereof. The upper end portion of the cylindrical body 71 is closed by a lid portion 71f, and a second opening 71b is provided at the horizontal center of the lid portion 71f. In addition, a third opening 71c is provided at the upper portion of the cylindrical body 71.

The abovementioned separator 70 is provided in the flow path of the suction duct 41 in the same way as the spirally wound pipe 64 according to the abovementioned embodiment. Specifically, the third opening 71c is connected to the pipe end 41c (FIG. 3A) on the upstream side of the suction duct 41, and the second opening 71b is connected to the pipe end 41d (FIG. 3A) on the downstream side of the suction duct 41. Further, the first opening 71a is connected to the abovementioned re-supply path 66 via an appropriate pipe 72.

The cyclone separator 70 configured in this way separates and recovers the SAP in the following way.

First, the air flow 4 of the suction duct 41 flows from the third opening 71c toward the inner circumferential surface of the cylindrical body 71 in a spiral pattern along the circumferential direction of the cylindrical body 71. The large SAP in the air flow 4 then falls under its own weight as it turns along an inside wall surface 71w of the cylindrical body 71. Then, the large SAP reaches the first opening 71a at the bottom, and is fed through the first opening 71a toward the re-supply path 66. By contrast, the lightweight SAP powder and the pulp fiber are carried by upward air currents generated in the horizontal center of the cylindrical body 71. Then, the lightweight SAP powder and the pulp fiber are exhausted from the second opening 71b of the lid portion 71f toward the suction duct 41. Thus, the large SAP is separated from the SAP powder and fed through the re-supply path 66 into the scattering duct 31.

Other Embodiments

While an embodiment of the present invention has been described above, the present invention is not limited to that embodiment and the following modifications are possible.

In the above embodiment, the connection of the branched pipe 65 of the centrifugal separator 63 to the re-supply path 66 is described. However, the invention is not limited to thereto. For example, the branched pipe 65 may be connected to the SAP supply path 56 and the recovered large SAP may be returned to the SAP flowing in the SAP supply path 56. However, separate systems as described in the above embodiment are preferred since it is difficult to control the supply amount of the SAP in the scattering duct 31 if the recovered large SAP is mixed therein.

In the above embodiment, the forming molds 21 formed in a concave shape on the outer circumferential surface 20a of the rotating drum 20 are described as an example of the deposition part. However, the invention is not limited as such. The following configuration may be employed: the outer circumferential surface 20a has a substantially smooth surface; the suction holes 22 are formed only in certain regions on the outer circumferential surface 20a; their drawing force acts so that the pulp fiber 2 and the SAP are deposited in those certain regions which serve as deposition parts; and thereby the absorbent 1 is formed. Moreover, a conveyor chain, a conveyor belt or the like may be used in place of the rotating drum 20. Specifically, the following configuration may be employed: the forming molds 21 is moved by the conveyor in a certain circumferential track and at a certain position on the track the scattering duct 31 is arranged.

In the above embodiment, the pulp fiber 2 (pulp pulverized into fibers) is described as a liquid absorbent fiber. However, any type of fiber that can be used for the absorbent 1 of an absorbent article, such as a conventional sanitary napkin or disposable diaper, may be used as the liquid absorbent fiber without any particular limitation. For example, a cellulosic short fiber such as rayon fiber or cotton fiber, or a synthetic short fiber of polyethylene or the like may be used. These fibers may be used alone or in a combination of two or more types.

A specific example of the SAP has been described in detail in the above embodiment. Any types of SAP that can be used for the absorbent 1 of an absorbent article, such as the conventional sanitary napkin or disposable diaper, may be used as the SAP without particular limitation. For example, various types of SAP such as a starch-based, a cellulosic, or a synthetic polymer SAP may be used. The SAP herein is normally a particulate. SAP having a liquid absorbency retaining force of at least 20 times its own weight and having a gelation property is preferred, and, for example, a starch acrylic acid (salt) graft copolymer, a starch acrylonitrile copolymer saponifier, cross-linked sodium carboxymethylcellulose, or an acrylic acid (salt) polymer is preferable. These SAPs may be used alone or in a combination of two or more types.

LIST OF REFERENCE NUMERALS

1: absorbent, 2: pulp fiber, 3: air flow,
4: air flow, 5: air flow, 6: air flow, 7: air flow,
9: sheet component, 10: fiber deposition device (manufacturing device), 10a: manufacturing device,
20: rotating drum, 20a: outer circumferential surface, 20b: circular wall,
21: forming mold (deposition part), 22: suction hole, 27: partition wall,
31 scattering duct, 31a: scattering opening, 31b: upper end opening,
41: suction duct, 41a: suction opening,
41c: pipe end on upstream side, 41d: pipe end on downstream side,
41e: portion,
50: SAP supply device,
51: normal supply system, 53: hopper (reservoir), 53a: bottom opening,
54: screw feeder, 55: chute,
56: SAP supply path,
56a: one tube end, 56b: other tube end,
57: nozzle, 58: blower,
61: recovery supply system,
63: centrifugal separator (separator),
64: spirally wound pipe, 64a: one end opening, 64b: other end opening,
65: branched pipe (branched path),
66: re-supply path, 66a: one tube end, 66b: other tube end,
67: nozzle,
68: throttle,
70: separator, 71: cylindrical tube, 71a: first opening,
71b: second opening, 71c: third opening,
71f: lid portion, 71w: inside wall surface, 72: pipe,
101: conveyor belt
S: substantially closed space, Z1: first zone, Z2: second zone,
C20: rotating shaft, C80: rotating shaft,
P41: certain position, Pj: joint position, P66: position,
SAP: super absorbent polymer

The invention claimed is:

1. An absorbent manufacturing device that forms an absorbent by depositing a liquid absorbent fiber and a super absorbent polymer in a deposition part, the device comprising:
a plurality of suction holes that are provided in the deposition part and cause the liquid absorbent fiber and the super absorbent polymer to be deposited in the deposition part by suction, the liquid absorbent fiber and the super absorbent polymer flowing inside a scattering duct;
a suction duct that is provided in communication with the suction holes and draws air so that the suction holes perform suction; and
a separator that separates a super absorbent polymer of size equal to or larger than a certain size from a flow of air flowing in the suction duct and returns the separated super absorbent polymer to the scattering duct, wherein
the separator is a centrifugal separator,
the centrifugal separator includes a flow channel that is provided as a part of the suction duct and has a spiral turning-radius, and
the flow channel has a branched path that is provided in a portion of the flow channel radially outwardly with respect to a radial direction of the spiral turning-radius, wherein
the super absorbent polymer having a size equal to or larger than a predetermined size is moved toward the portion of the flow channel and is guided into the branched path by the centrifugal force that acts while flowing through the flow channel; and
the super absorbent polymer of the predetermined size is fed to the scattering duct through the branched path.

2. An absorbent manufacturing method that forms an absorbent by depositing a liquid absorbent fiber and a super absorbent polymer in a deposition part, the method comprising:
depositing the liquid absorbent fiber and the super absorbent polymer in the deposition part by suction from a plurality of suction holes, the suction holes being provided in the deposition part, the liquid absorbent fiber and the super absorbent polymer flowing inside a scattering duct; and
when the suction holes suck an air by suction of the air of a suction duct that is provided in communication with the suction holes,
separating a super absorbent polymer of size equal to or larger than a certain size from an air flowing through the suction duct using a separator and
returning the separated super absorbent polymer to the scattering duct, wherein
the separator is a centrifugal separator,
the centrifugal separator includes a flow channel that is provided as a part of the suction duct and has a spiral turning-radius, and
the flow channel has a branched path that is provided in a portion of the flow channel radially outwardly with respect to a radial direction of the spiral turning-radius, wherein
the super absorbent polymer having a size equal to or larger than a predetermined size is moved toward the portion of the flow channel and is guided into the branched path by centrifugal force that acts while flowing through the flow channel, and
the super absorbent polymer of the predetermined size is fed to the scattering duct through the branched path.

* * * * *